United States Patent [19]

Muraki et al.

[11] Patent Number: 5,003,984

[45] Date of Patent: Apr. 2, 1991

[54] APPARATUS FOR ALERTING A DOCTOR BY RADIO TO PROVIDE AN ALARM FOR A PATIENT

[75] Inventors: Yoshiya Muraki; Hiroyuki Koike, both of Tokyo, Japan

[73] Assignee: Fukuda Densky Co, Ltd., Tokyo, Japan

[21] Appl. No.: 473,061

[22] Filed: Jan. 31, 1990

[30] Foreign Application Priority Data

Oct. 23, 1989 [JP] Japan .............................. 1-123851[U]

[51] Int. Cl.$^5$ ................................................ A61B 5/04
[52] U.S. Cl. ..................... 128/710; 128/903; 128/904; 128/696
[58] Field of Search ............... 128/696, 668, 710, 903, 128/904

[56] References Cited

U.S. PATENT DOCUMENTS

| | | | |
|---|---|---|---|
| 4,068,096 | 1/1978 | Rattenborg et al. | 128/904 |
| 4,141,351 | 2/1979 | James et al. | 128/904 |
| 4,319,241 | 3/1982 | Mount | 128/903 |
| 4,827,943 | 5/1989 | Bornn et al. | 128/668 |
| 4,883,064 | 11/1989 | Olson et al. | 128/696 |

Primary Examiner—Francis Jaworski
Assistant Examiner—George Manuel
Attorney, Agent, or Firm—Sughrue, Mion, Zinn, Macpeak & Seas

[57] ABSTRACT

An apparatus for alerting a doctor which provides an alarm corresponding to a patient, and receives living body information signals transmitted through a transmitter. The apparatus alerts a doctor with a buzzer sound or a vibration indicating that the condition of the patient and of the living body information signals has changed suddenly. The apparatus includes a portable casing having a front plate, a rear plate, a top plate, a bottom plate, a left plate, and a right plate. The casing is provided with a circuit plate on which an electric circuit is mounted which receives and treats the living body information signals. Moreover, the apparatus is provided with a display portion provided on the casing and connected with the electric circuit. The wave form of at least an electrocardiogram signal included in the living body information signals is displayed on the display portion.

10 Claims, 5 Drawing Sheets

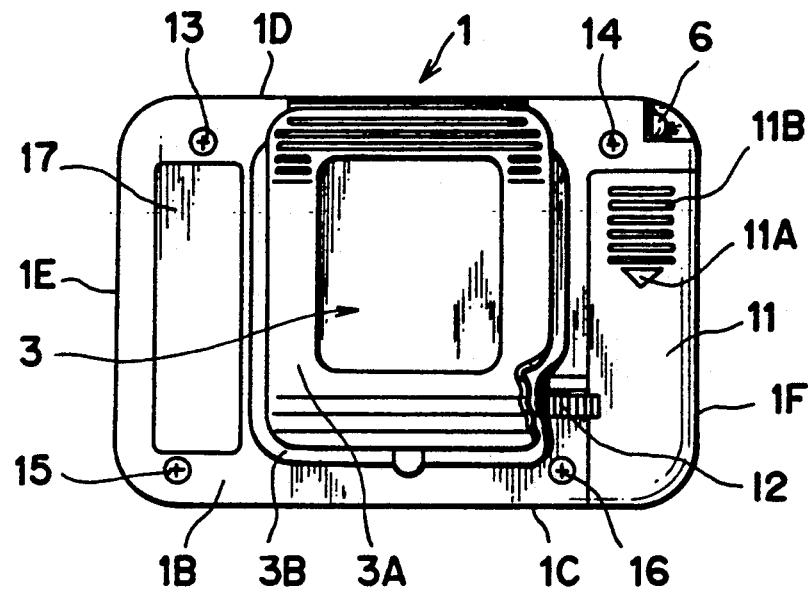
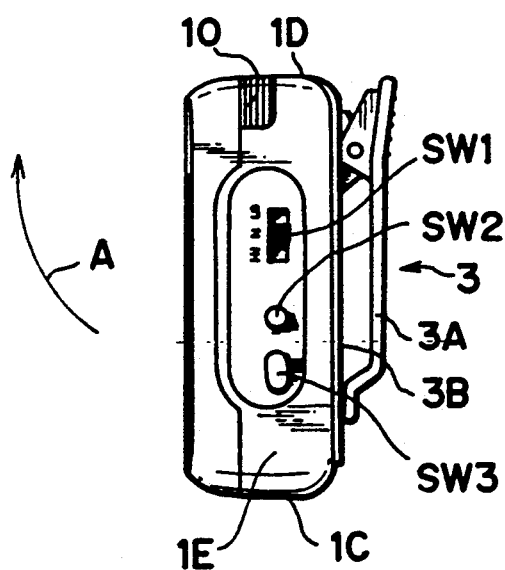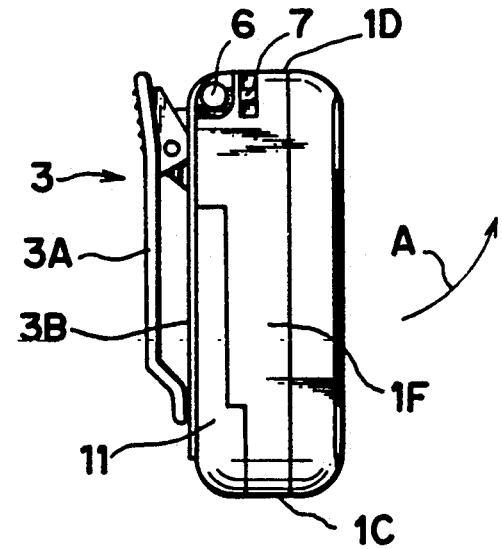

APPARATUS FOR ALERTING A DOCTOR BY RADIO TO PROVIDE AN ALARM FOR A PATIENT

BACKGROUND OF THE INVENTION

1. Field of the Invention

The present invention relates to an apparatus for alerting a doctor by radio to provide an alarm for a patient.

More particularly, it relates to an apparatus for alerting a doctor by radio to give an alarm for a patient, in which the wave form of the electrocardiogram signal of the patient is displayed.

2. Description of the Related Art

Generally, in a hospital, a doctor has a portable receiver for being alerted by radio when the condition of a patient has changed suddenly.

For example, a few doctors typically watch the condition of many patients with heart disease during the night in a hospital.

Hence, when the doctor gives his full time to one patient, he cannot know that the condition of another patient has changed suddenly.

In order to avoid such an inconvenience, the doctor carries a portable receiver to alert him when an alarm for a patient is given.

A conventional apparatus for alerting a doctor by radio, has a display portion wherein only messages are displayed.

For example, a message "PATIENT ALARM NO.=5" is displayed.

A doctor, who has seen the message, thinks that the condition of the fifth patient has changed suddenly, and accordingly, he immediately goes to and takes action for this patient.

However, the above message "PATIENT ALARM NO.=5" has been displayed such that a system for monitoring a patient located in a hospital mechanically judges the condition of the patient.

Hence, though the patient's mere turning over in bed changes the direction of his heart, whereby the wave of his electrocardiogram changes, the system sometimes judges that the condition of the patient has been changed suddenly.

The result is occasionally that the above message is displayed.

And, though electrodes fitted to the breast of the patient are taken off, thereby the wave form of his electrocardiogram changes, the system sometimes judges that the condition of the patient has been changed suddenly.

The result is occasionally that the above message is displayed.

These two cases are instances that an erroneous judgement of the system causes the above patient alarm message to be displayed.

Hence, although the doctor has quickly gone to the patient, there is usually no need to take any action for the patient.

That is to say, since the doctor cannot judge whether or not the condition of the patient has been changed suddenly by viewing the display, it appears that he should take action for his patient due to a mistaken message.

SUMMARY OF THE INVENTION

An object of the present invention is to allow a doctor to judge precisely whether or not the condition of a patient has changed suddenly using an apparatus which alerts the doctor of a possible sudden change in the patient's condition.

The above-mentioned object can be achieved by an apparatus for alerting a doctor by radio to provide an alarm corresponding to a patient, which receives a living body information signal transmitted through a transmitter and alerts the doctor with a buzzer sound or a vibration indicating that the condition of the patient and of the living body information signal has been changed suddenly. The apparatus includes a portable casing having a front plate, a rear plate, a top plate, a bottom plate, a left plate, and a right plate. The casing is provided with a circuit plate, on which circuit plate an electric circuit is mounted so as to receive and treat the living body information signals, and a display portion being furnished on the casing and being connected with the electric circuit, on which display portion the wave form of at least an electrocardiogram signal of the living body signals is displayed.

BRIEF DESCRIPTION OF THE DRAWINGS

Further features and advantages of the present invention will be apparent from the following description with reference to the accompanying drawings, wherein:

FIGS. 2A to 2E are detailed drawings of the embodiment of the present invention.

DESCRIPTION OF THE PREFERRED EMBODIMENTS

Figure 1:
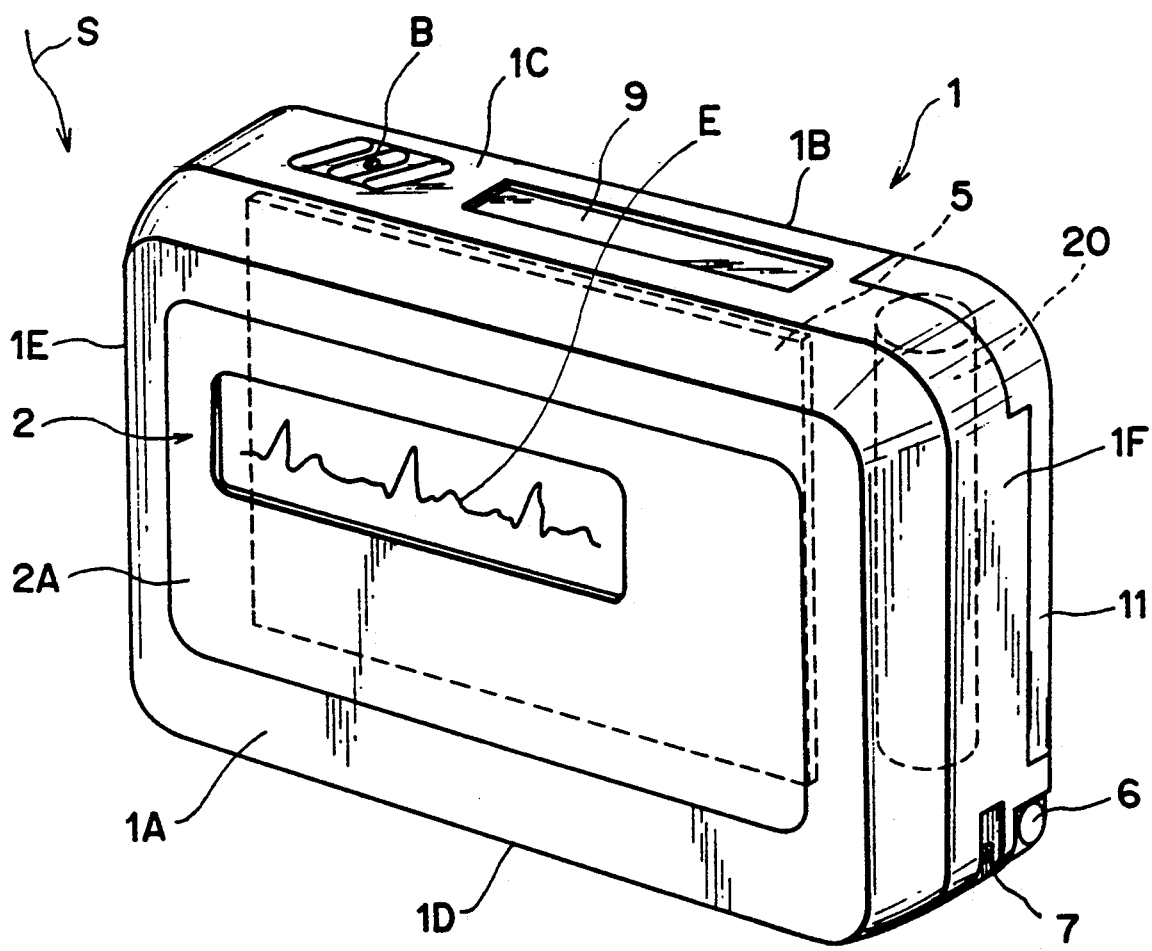
FIG. 1 is a whole drawing of an embodiment of the present invention.

FIG. 1 is a whole drawing of an embodiment of the present invention, wherein reference numeral 1 shows a casing. 2 a display portion. 5 a circuit plate, 6 a mounting pin, 7 a bar, 8 an opening, and 9 a groove.

The casing 1 has wholly the shape of a rectangular parallelepiped, and is formed by an insulator, for example, plastics.

The casing 1 is so small that it has a width of 105 mm, a height of 74.5 mm, and a thickness of 30 mm.

Figure 4:
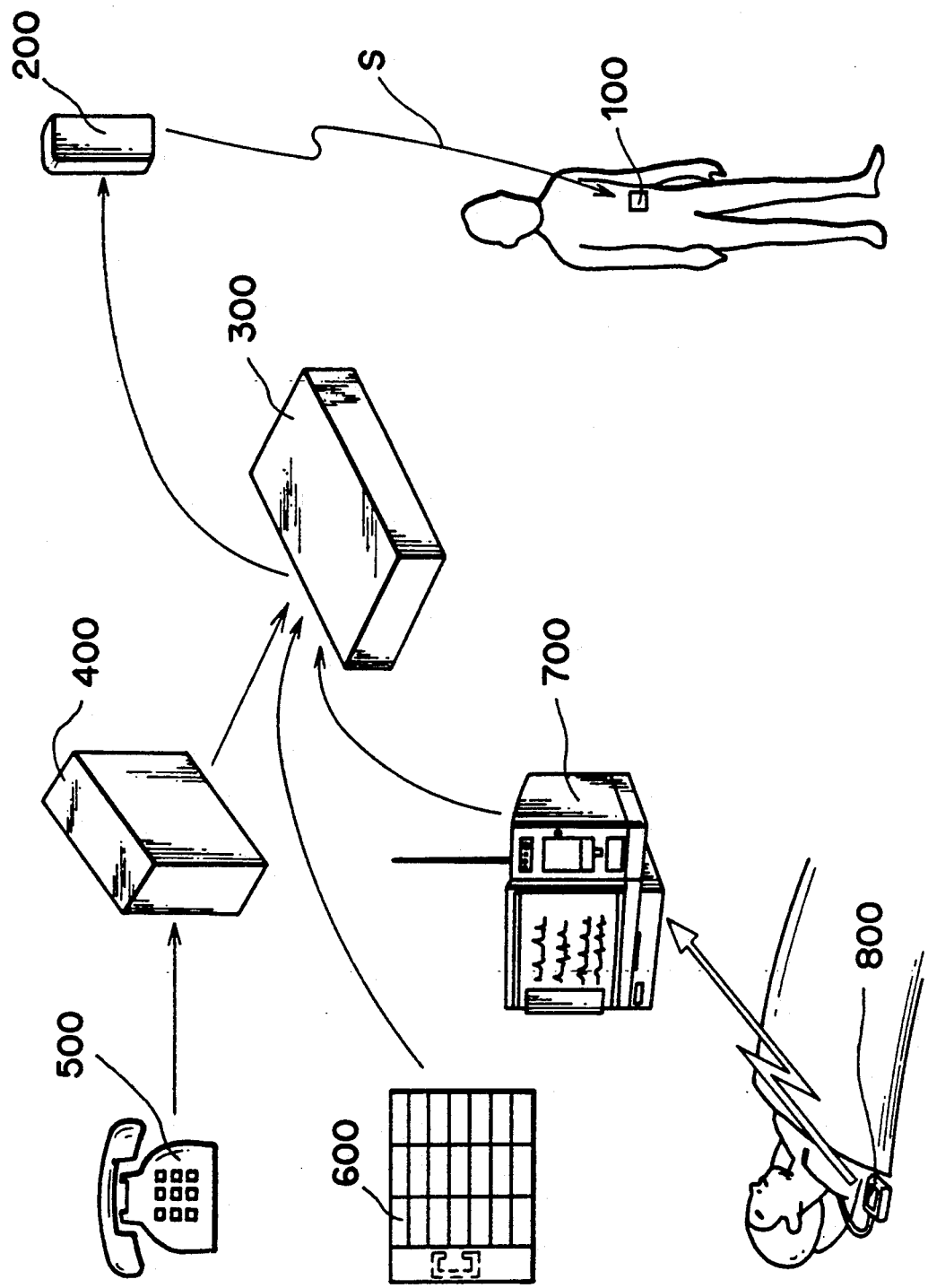
FIG. 4 is a drawing of an application of the present invention.

The casing 1 has a circuit plate 5 within, on which circuit plate 5 an electric circuit is loaded so as to receive and treat living body information signals S transmitted by radio from a transmitter 200 (See FIG. 4).

The above electric circuit can be operated, for example, by an alkali-manganese dry cell 20, which dry cell 20 has a 3 unit size and electromotive force of 1.5 V.

A display portion 2 is mounted at the upper area on the front plate IA of the casing 1, which display portion 2 is formed by liquid crystal, for example, and is protected by a protecting plate 2A with transparency and is made of plastics.

On the display portion 2, at least the wave form E of a patient's electrocardiogram, and many other living body information signals S. may be displayed, when a patient alarm occurs, that is to say, when the condition of the patient has been changed suddenly.

On the display portion 2, except for the above wave form E. messages composed of English or numeral characters, for example the message "PATIENT ALARM NO.=5". are also displayed as in the prior art.

Light may be emitted from the back surface of the display portion 2 so that the wave form E of the patient's electrocardiogram or messages in the dark area may easily be seen.

FIGS. 2A to 2E are detailed drawings of an embodiment of the present invention.

Figure 2A:
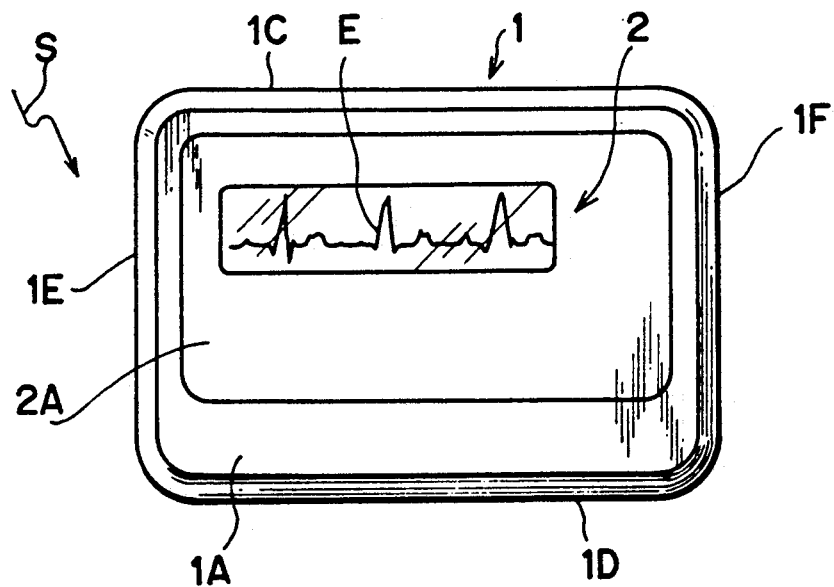
Figure 2B:
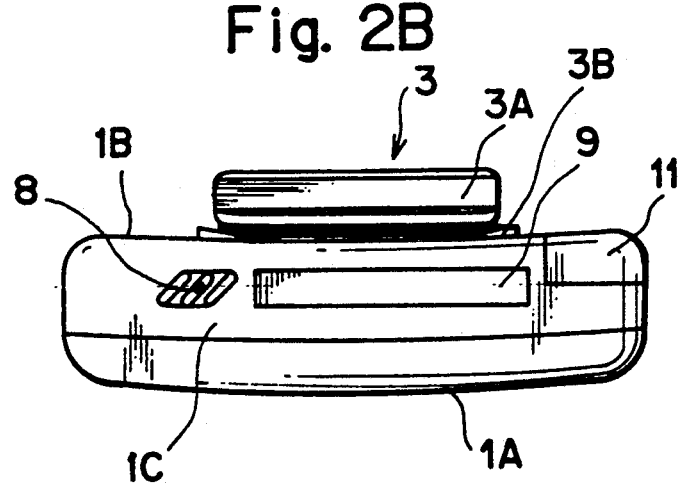

FIGS. 2A is a front view, FIG. 2B a top view. FIG. 2C a rear view, FIG. 2D a left side view, and FIG. 2E a right side view.

The opening 8 is formed on the top plate 1C of the casing 1, through which opening 8 buzzer sound is output so as to alert a doctor.

Moreover, on the top plate 1C of the casing 1, the groove 9 is formed, in which groove 9 a stamp tape may be stuck.

A doctor may be alerted not only by a buzzer sound, but also by vibration as described hereinafter, which both are interchangeable with each other.

A rear plate 1B is fixed to the casing 1 with screws 13. 14. 15 and 16.

A belt clip 3 is mounted pivotally on the middle area of the rear plate 1B. a place 17 for sticking a label with an owner s name etc. is formed on the left area of the same plate 1B, and a battery cover 11 is situated on the right area of the same plate 1B.

The battery cover 11 may be mounted and demounted with a claw 12 for locking, on which battery cover 11 projections 11A and 11B are formed so as to easily operate it.

Figure 3A:
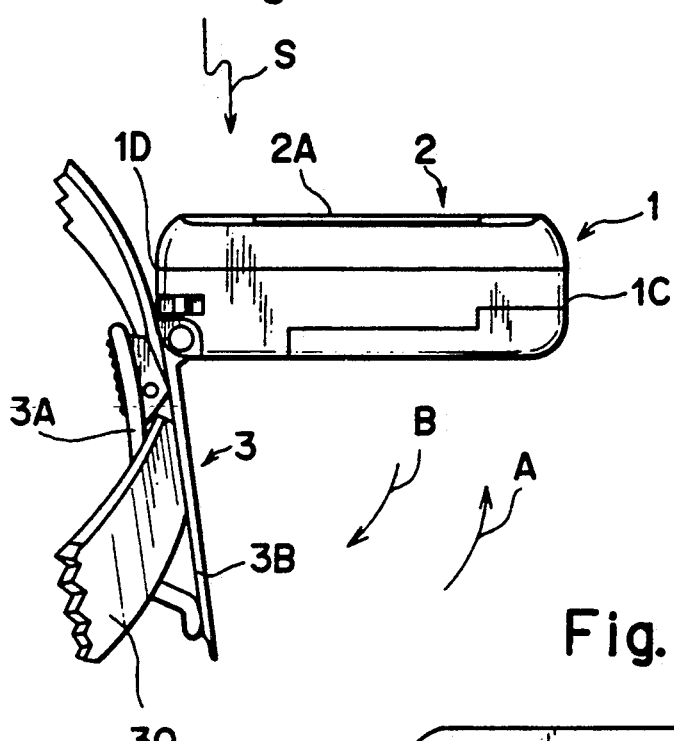
FIGS. 3A to 3C are explanatory drawings of the operation of the present invention.

The belt clip 3 has a first member 3A and a second member 3B (see FIG. 2D and 2E). which members 3A and 3B are energized with a spring so as to hold a belt 30 (see FIG. 3A).

Figure 3B:
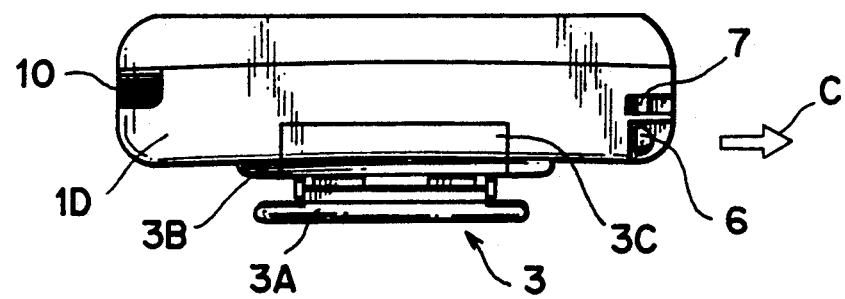

The second member 3B is mounted pivotally on the casing 1, through a mounting portion 3C (see FIG. 3B).

The belt clip 3 may be taken off from the casing 1, by means of pulling the mounting pin 6 to the right direction (see FIGS. 2C and 3B). Thereafter, a stand plate 4 may be mounted instead of the belt clip 3 (see FIG. 3C).

A receiving lamp 10 is installed on the left plate 1E of the casing 1, from the lower area thereof through the bottom plate 1D, which receiving lamp 10 goes on and off when the above-mentioned wave form E of an electrocardiogram and other messages are received.

A first switch SW1, a second switch SW2, and a third switch SW3 are respectively furnished in order on the middle area of the left plate 1E.

When the first switch SW1 is in the LO position, an electric source in the casing 1 is turned off and the data stored in a memory is erased from the memory.

When the first switch SW1 is in the N position as shown in FIG. 2D. a doctor may be alerted with vibration. When it is in the HI position, he may be alerted with a buzzer sound.

The second switch SW2 is one which switches on a light for irradiating the display portion 2.

The functions of the third switch SW3 are as follows.

That is to say, it stops the buzzer sound or the vibration, changes a picture to be displayed on the display portion 2, as to the wave form E of the patient's electrocardiogram or messages, displays the contents of data stored in the memory, and clears the contents displayed on the display portion 2 when it is pushed continuously, etc.

The above-mentioned mounting pin 6 and the bar 7 are furnished respectively, from the lower area of the right plate 1F through the bottom plate 1D.

A chain clip is wound around bar 7 to prevent the casing 1 from falling down when it is put in a pocket, etc.

The operation of the present invention will be described hereinafter with reference to FIGS. 3A to 3C.

The belt 30 is gripped with the first member 3A and second member 3B constituting the belt clip 3, whereby an apparatus for alerting a doctor by radio in accordance with the present invention may be mounted on the human body, as shown in FIG. 3A.

When the condition of a patient has suddenly changed, a buzzer sound or vibration alerts a doctor. Additionally, the wave form E of the patient's electrocardiogram is displayed on the display portion 2.

The casing 1 is pivoted by 90° to the direction shown by an arrow A. whereby the wave form E can be observed clearly.

The third switch SW3 is pushed, whereby the name of the patient having the wave form E is displayed on the display portion 2.

Accordingly, the doctor can judge precisely whether or not the condition of the patient with the wave form E displayed has actually changed suddenly.

When it is unnecessary to look at the display portion 2, the casing 1 is pivoted to the direction shown by an arrow B. whereby it is returned to the original position, as shown in FIG. 3A.

Figure 3C:
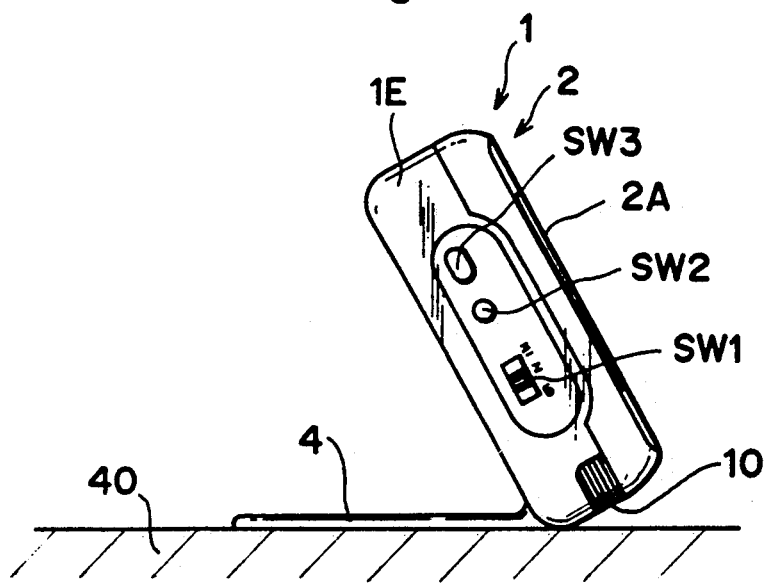

The belt clip 3 may be demounted by moving the mounting pin 6 in the direction shown by the arrow C of FIG. 3B. whereby the stand plate 4 can be mounted instead of the belt clip 3, as shown in FIG. 3C.

The stand plate 4 has the effect that the wave form E shown on the display portion 2 can be observed by standing the apparatus in accordance with the present invention on a desk 40, for example, as shown in FIG. 3C.

FIG. 4 is a drawing of an application of the present invention, wherein reference numeral 100 is the apparatus in accordance with the present invention, 200 a transmitter. 300 a controller. 400 a private branch exchange (PBX). 500 a telephone. 600 a nurse caller, 700 a monitor, and 800 an electrocardiogram (ECG) telemeter.

The transmitter 200 is an apparatus which modulates signals output from the controller 300 and transmits them to the apparatus 100 in accordance with the present invention as the living body information signals S.

The controller 300 is an apparatus which treats signals output from the PBX 400, the nurse caller 600, or the monitor 700, and smoothly connects these apparatuses with the transmitter 200.

The PBX 400 is an apparatus which connects the telephone 500 with an internal telephone extension or with an outside telephone line.

The nurse caller 600 is an apparatus in which a nurse pushes the switch corresponding to the name of the specific patient, thereby the sudden change of the patient's condition is known to a doctor.

The monitor 700 is an apparatus which keeps watch on an electrocardiogram etc. of a patient whose condition may suddenly change.

The ECG telemeter 800 is an apparatus which modulates electrocardiogram signals led out from the living body of a patient and transmits it to the monitor 700.

As is apparent from FIG. 4, the apparatus 100 in accordance with the present invention may be applied when a doctor will be alerted by using, for example, the telephone 500, the nurse caller 600, and the monitor 700.

That is to say, the apparatus 100 may be linked with the telephone 500, the nurse caller 600, and the monitor 700, respectively.

The linkage with the telephone 500 is a personal call for calling one specific person, or a group call for calling one specific group, etc.

The linkage with the nurse caller 600 is an instance where a doctor may be alerted by pushing the switch, as described hereinbefore, in the nurse caller 600.

The linkage with the monitor 700 is an instance where a doctor may be alerted by displaying the wave form E of the specific patient's electrocardiogram signal on the display portion 2, as described already.

According to the present invention, even if the patient monitoring system outputs an erroneous patient alarm message, a doctor can guess roughly the condition of a patient by observing the wave form E of the patient's electrocardiogram signal displayed on the display portion 2.

Hence, the present invention has the effect that a doctor can judge precisely, with an apparatus which alerts him by radio transmission, whether or not the condition of a patient has suddenly changed.

We claim:

1. An apparatus for alerting a doctor which provides an alarm corresponding to a patient by receiving living body information signals S transmitted by radio through a transmitter and providing said doctor with a buzzer sound or a vibration to indicate that the condition of the patient corresponding to the living body information signals S has suddenly changed, said apparatus comprising:
   a portable casing having a front plate, a rear plate connected to positioning means for positioning said casing, a top plate, a bottom plate, a left plate, and a right plate;
   a circuit plate provided within said casing;
   an electric circuit mounted on said circuit plate for receiving said living body information signals S transmitted by radio from said transmitter; and
   display means provided on said casing and connected with said electric circuit, said display means displaying said living body information signals S received by said electric circuit, said displayed living body information signals S including at least a wave form E of electrocardiogram signals.

2. An apparatus for alerting a doctor according to claim 1, wherein said display means is provided on said front plate of said casing, and is formed by liquid crystal.

3. An apparatus for alerting a doctor according to claim 1, wherein said positioning means is a belt clip mounted pivotally on said rear plate of said casing.

4. An apparatus for alerting a doctor according to claim 1, wherein said positioning means is a stand plate mounted pivotally on said rear plate of said casing.

5. An apparatus for alerting a doctor according to claim 1, wherein said positioning means is either a belt clip or a stand plate interchangeably attached to said casing 1.

6. An apparatus for alerting a doctor according to claim 1, further comprising:
   a receiving lamp for indicating receipt of a radio message, said receiving lamp installed between the lower area of said left plate and said bottom plate; and
   a first switch SW1, a second switch SW2, and a third switch SW3 provided in a central area of said left plate.

7. An apparatus for alerting a doctor according to claim 6, wherein:
   said first switch SW1 controls a power supply to said apparatus and distinguishes whether the buzzer sound or vibration is to be used to alert the doctor when the power is on;
   said second switch SW2 switches on a light for irradiating a background portion of said display means; and
   said third switch controls provision of the name of a patient whose wave form E is being displayed on said display means.

8. An apparatus for alerting a doctor according to claim 1, wherein a mounting pin and a bar are provided between the lower area of said right plate and said bottom plate.

9. An apparatus for alerting a doctor according to claim 1, said top plate of said casing including:
   an opening through which said buzzer sound is provided; and
   a groove through which a tape stamped with the name of said doctor is provided.

10. An apparatus for alerting a doctor according to claim 1, wherein said transmitter receives said living body information signals S from either a telephone private branch exchange, a nurse caller, or a monitor.

* * * * *